US012682297B2

(12) United States Patent
Zhao et al.

(10) Patent No.: US 12,682,297 B2
(45) Date of Patent: Jul. 14, 2026

(54) METHOD, SYSTEM AND STORAGE MEDIUM FOR ASSESSING AND TRAINING PERSONNEL SITUATIONAL AWARENESS

(71) Applicant: KINGFAR INTERNATIONAL INC., Beijing (CN)

(72) Inventors: Qichao Zhao, Beijing (CN); Ran Yang, Beijing (CN)

(73) Assignee: KINGFAR INTERNATIONAL INC., Beijing (CN)

( * ) Notice: Subject to any disclaimer, the term of this patent is extended or adjusted under 35 U.S.C. 154(b) by 218 days.

(21) Appl. No.: 18/239,148

(22) Filed: Aug. 29, 2023

(65) Prior Publication Data

US 2024/0070575 A1     Feb. 29, 2024

(30) Foreign Application Priority Data

Aug. 29, 2022     (CN) .......................... 202211050430.5

(51) Int. Cl.
   *G06Q 10/0631*     (2023.01)
   *A61B 5/16*     (2006.01)
(52) U.S. Cl.
   CPC ...... *G06Q 10/063112* (2013.01); *A61B 5/165* (2013.01)
(58) Field of Classification Search
   CPC ....... G06Q 10/063112; G06Q 10/0631; G06Q 10/06; A61B 5/165; A61B 5/16; A61B 5/01
   See application file for complete search history.

(56) References Cited

U.S. PATENT DOCUMENTS

2018/0315063 A1* 11/2018 Cheesman ............. G06V 40/70
2019/0046099 A1*  2/2019 Lee ...................... A61B 5/0035
(Continued)

FOREIGN PATENT DOCUMENTS

CN       104605820 A     5/2015
CN       114020185 A     2/2022
(Continued)

OTHER PUBLICATIONS

Paul Pope, "Evaluation & Accountability Collaborative Quick Tip Series for Extension Faculty Conducting Evaluations", AgriLIFE Extension, Texas A&M System, Published on Jul. 4, 2022. (Year: 2022).*

(Continued)

*Primary Examiner* — Timothy Padot
*Assistant Examiner* — Gabriel Jose Torres Chanza
(74) *Attorney, Agent, or Firm* — Cooper Legal Group, LLC

(57)     ABSTRACT

The present application provides a method, system, and storage medium of personnel situational awareness evaluation and training, the method comprises: obtaining situational awareness scenes and tasks; performing the personnel situational awareness testing or training through the situational awareness task in the situational awareness scene, obtaining an objective data for each dimension of a plurality of situational awareness tasks collected by personnel based on a plurality of sensing devices during an implementation of the situational awareness tasks, obtaining subjective evaluation results of the personnel after the situational awareness testing or training; a multiple regression analysis is performed based on the objective data and the subjective evaluation results of each dimension of each situational awareness task to obtain a single task and single dimension evaluation result, a single task and total task (Continued)

obtaining a situational awareness scene, and obtaining situational awareness tasks constructed under the situational awareness scene, wherein the situational awareness tasks comprises a plurality of types of a perception task, a comprehension task, a prediction task, and a decision task — S100 performing a personnel situational awareness testing or training situational awareness with the situational awareness tasks in the situational awareness scene, and obtaining an objective data for each of dimensions of a plurality of situational awareness tasks collected by a plurality of sensing devices during performing, by an personnel, of the situational awareness tasks, and obtaining subjective evaluation results for the personnel after the situational awareness testing or training; wherein the dimensions comprises a plurality of types of a physiological dimension, a brain cognitive activity dimension, a behavioral dimension, and a behavioral paradigm dimension — S200 performing a multiple regression analysis on the objective data for each of dimensions of a plurality of situational awareness tasks and the subjective evaluation results to obtain a single task and single dimension evaluation result of the situational awareness tasks, weighting the single task and single dimension evaluation result to obtain a single task evaluation result, and weighting the single task evaluation result to obtain a total task evaluation result — S300 determining whether the personnel needs the situational awareness training according to the single task evaluation result or the total task evaluation result, and after each personnel situational awareness training is completed, reviewing the personnel situational awareness training by comparing the single task evaluation result or the total task evaluation result of a plurality of historical moments — S400 evaluation results of the situational awareness task; after each personnel situational awareness training, reviewing the personnel situational awareness training.

9 Claims, 4 Drawing Sheets

(56) References Cited

U.S. PATENT DOCUMENTS

| | | | | |
|---|---|---|---|---|
| 2020/0253527 | A1* | 8/2020 | Ellison | A61B 5/165 |
| 2020/0367789 | A1* | 11/2020 | Moffat | A61B 5/7275 |
| 2021/0043011 | A1 | 2/2021 | Gates | |
| 2021/0391088 | A1* | 12/2021 | Harrah | A61B 5/01 |
| 2022/0061678 | A1* | 3/2022 | Schulhauser | A61B 5/165 |
| 2022/0133194 | A1* | 5/2022 | Bach | A61B 5/6801 |
| | | | | 600/544 |

FOREIGN PATENT DOCUMENTS

| | | |
|---|---|---|
| CN | 114469089 A | 5/2022 |
| WO | WO-2008064431 A1 * | 6/2008 ........... A61B 5/7267 |
| WO | WO-2021138185 A1 * | 7/2021 ............... G06N 7/01 |

OTHER PUBLICATIONS

Luke Petersen, Lionel Robert, X. Jessie Yang, and Dawn M. Tilbury, "Situational Awareness, Driver's Trust in Automated Driving Systems and Secondary Task Performance", SAE International Journal of Connected and Autonomous Vehicles, Accepted for Publication on Feb. 20, 2019. (Year: 2019).*
European Search Report for corresponding European patent Application No. 23193688.1, dated Jan. 22, 2024, 5 pages.
Oberhauser, Matthias, et al., "Bridging the Gap Between Desktop Research and Full Flight Simulators for Human Factors Research", Jul. 21, 2015, Topics in Cryptology—CT-RSA 2020: The Cryptographers' Track at the RSA Conference 2020, pp. 460-471, XP047537972.
Grundmann, Robert, et al., "Increasing Maritime Situational Awareness by Augmented Reality Solutions", retrieved Jan. 11, 2024, URL: https://www.cml.fraunhofer.de/content/dam/cml/en/documents/Studien/Burmeister%20Grundmann%20Hohnrath%20Ujkani%20(2021)_Increasing-Situational-Awareness-by-Augmented-Reality-Solutions-White%20Paper.pdf, Feb. 28, 2022, pp. 1-44, XP093118141.

* cited by examiner obtaining a situational awareness scene, and obtaining situational awareness tasks constructed under the situational awareness scene, wherein the situational awareness tasks comprises a plurality of types of a perception task, a comprehension task, a prediction task, and a decision task — S100 performing a personnel situational awareness testing or training situational awareness with the situational awareness tasks in the situational awareness scene, and obtaining an objective data for each of dimensions of a plurality of situational awareness tasks collected by a plurality of sensing devices during performing, by an personnel, of the situational awareness tasks, and obtaining subjective evaluation results for the personnel after the situational awareness testing or training; wherein the dimensions comprises a plurality of types of a physiological dimension, a brain cognitive activity dimension, a behavioral dimension, and a behavioral paradigm dimension — S200 performing a multiple regression analysis on the objective data for each of dimensions of a plurality of situational awareness tasks and the subjective evaluation results to obtain a single task and single dimension evaluation result of the situational awareness tasks, weighting the single task and single dimension evaluation result to obtain a single task evaluation result, and weighting the single task evaluation result to obtain a total task evaluation result — S300 determining whether the personnel needs the situational awareness training according to the single task evaluation result or the total task evaluation result, and after each personnel situational awareness training is completed, reviewing the personnel situational awareness training by comparing the single task evaluation result or the total task evaluation result of a plurality of historical moments — S400

FIG. 1 input layer      hidden layer      output layer

METHOD, SYSTEM AND STORAGE MEDIUM FOR ASSESSING AND TRAINING PERSONNEL SITUATIONAL AWARENESS

CROSS-REFERENCE TO RELATED APPLICATION

The present application is based on and claims the priority benefits of China application No. 202211050430.5, filed on Aug. 29, 2022. The entirety of China application No. 202211050430.5 is hereby incorporated by reference herein and made a part of this specification.

TECHNICAL FIELD

The present application relates to a technical field of a virtual reality interaction and simulation interaction, and in particular, relates to a method, system and storage medium for assessing and training personnel situational awareness.

BACKGROUND ART

Situational awareness refers to a person's ability to perceive environmental changes accurately and predict future development through understanding and judgment during an information processing. In the fields of sports, military industry and national defense, aerospace and so on, there is a need for a personnel situational awareness evaluation and training, however, with an improvement of the demand and an updating and iteration of a technology, an existing situational awareness measurement, evaluation, or detection systems cannot meet rich situational needs.

A combination of the existing awareness evaluation and training is not sufficient, and applicable scenes are relatively limited, methods of the personnel situational awareness evaluation are not scientific and reasonable enough. For example, in some existing technologies, a pilot situational awareness level is mainly predicted with typical dynamic scenes composed of a plurality of clue interfaces and task operations, but the present application limits the personnel to the pilot, and the scenes also have certain limitations, and does not propose combining multi-dimensional data for scientific and reasonable evaluation.

Therefore, how to provide a method of combining the evaluation with the training process to the personnel situational awareness evaluation and training, which application scenes are flexible, and the situational awareness evaluation is scientific and reasonable, and it is an urgent problem to be solved.

SUMMARY

In response to the problems existing in the prior art, the purpose of the present application is to provide a method and system for assessing and training personnel situational awareness, which aims to provide a method, system, and storage medium of combining the evaluation with the training process to the personnel situational awareness evaluation and training, which application scenes are flexible, and the situational awareness evaluation is scientific and reasonable.

In a first aspect, the present application provides a method for assessing and training personnel situational awareness, comprising:

obtaining a situational awareness scene, and obtaining situational awareness tasks constructed under the situational awareness scene, wherein the situational awareness tasks comprises a plurality of types of a perception task, a comprehension task, a prediction task, and a decision task;

performing a personnel situational awareness testing or training situational awareness with the situational awareness tasks in the situational awareness scene, and obtaining an objective data for each of dimensions of a plurality of situational awareness tasks collected by a plurality of sensing devices during performing, by a personnel, of the situational awareness tasks, and obtaining subjective evaluation results for the personnel after the situational awareness testing or training; wherein the dimensions comprises a plurality of types of a physiological dimension, a brain cognitive activity dimension, a behavioral dimension, and a behavioral paradigm dimension;

performing a multiple regression analysis on the objective data for each of dimensions of a plurality of situational awareness tasks and the subjective evaluation results to obtain a single task and single dimension evaluation result of the situational awareness tasks, weighting the single task and single dimension evaluation result to obtain a single task evaluation result, and weighting the single task evaluation result to obtain a total task evaluation result; and determining whether the personnel needs the situational awareness training according to the single task evaluation result or the total task evaluation result, and after each personnel situational awareness training is completed, reviewing the personnel situational awareness training by comparing the single task evaluation result or the total task evaluation result of a plurality of historical moments.

In some embodiments of the present application, the obtaining the situational awareness scene comprises building a custom scene or importing a third-party scene via a communication interface; and the obtaining the situational awareness task in the situational awareness scene comprises, in the situational awareness scene, importing the situational awareness tasks, or customizing the situational awareness tasks, or importing a behavioral paradigm that contains the situational awareness task scene.

In some embodiments of the present application, the customizing the situational awareness tasks comprises a full task setting and a single task setting; the full task setting comprises setting all of the situational awareness tasks at a freezing time point, and the single task setting comprises setting one of the situational awareness tasks at a freezing time point; and wherein, the freezing time point is a time point at which the situational awareness scene is paused for customizing the situational awareness tasks, number of the freezing time points is set to be one or more.

In some embodiments of the present application, the perception task comprises perceiving information of the situational awareness scene, and recording an initial state of the information of the situational awareness scene at a time of setting the perception task; the comprehension task comprises comprehending the information of the situational awareness scene, recording a correct option by obtaining a selection of custom setup question options at a time of setting the comprehension task; the prediction task comprises predicting the information of the situational awareness scene at a future moment and recording the information of the situational awareness scene at the future moment; and the decision task comprises making a decision for the information of the situational awareness scene and making a selection based on customized decisions.

In some embodiments of the present application, the method further comprises: inputting a situational awareness scene containing the situational awareness task as an input layer into a situational awareness task decision model, and outputting an optimal decision of the situational awareness task.

In some embodiments of the present application, the sensing devices comprise a physiological sensing device, an EEG sensing device, an infrared sensing device, and a behavioral response recording device; before performing the personnel situational awareness training, the method further comprises obtaining a frequency of the personnel situational awareness training; and the method further comprises grading the total task evaluation results and performing situational awareness training for the personnel below a preset level.

In some embodiments of the present application, the reviewing the personnel situational awareness training by comparing the single task evaluation result or the total task evaluation result at a plurality of historical moments comprises reviewing the personnel situational awareness training by calculating a training result comparison moment-on-moment to with a formula of:

$$C = (E'_i - E'_{i-1})/E'_{i-1} * 100\%$$

C represents a training evaluation result comparison moment-on-moment for each task or the total task, $$E'_i$$

is a training evaluation result of each task or the total task for an i-th training, a calculation of $$E'_i$$

is consistent with a calculation, by a situational awareness evaluation module, of the single task evaluation result or the total task evaluation result.

In some embodiments of the present application, the reviewing the personnel situational awareness training by comparing the single task evaluation result or the total task evaluation result at a plurality of historical moments further comprises reviewing the personnel situational awareness training with a linear regression coefficient; the linear regression coefficient is a coefficient calculated with an univariate linear regression equation for the comparison of the training evaluation result of each task or the total task training evaluation result The review of the single task evaluation result or the total task evaluation result can clearly and intuitively show an effectiveness of the training, making the setting of the training process more evidence-based and thereby improving an efficiency of the personnel situational awareness training.

In a second aspect, the present application provides a system for assessing and training personnel situational awareness, comprising: a processor and a memory, wherein the memory is configured to store computer instructions, the processor is configured to execute the computer instructions stored in the memory, and the system is configured to implement the method according to any one of the above embodiments when the computer instructions are executed by the processor.

In a third aspect, the present application provides non-transitory computer-readable storage medium with a computer program stored thereon, wherein the computer program is executed by a processor to implement the method according to any one of the above embodiments.

The present application relates to the method, system and storage medium of the personnel situational awareness evaluation and training. By obtaining different situational awareness scenes and the situational awareness tasks to flexibly change the scenes, obtaining a comprehensive score by progressively evaluating the results of the single task and single dimension evaluation, the single task evaluation, and the total task evaluation, achieving a scientific and reasonable evaluation of the personnel situational awareness, and combining the process of the evaluation and training, effectively expanding a functionality and application scope of the system.

BRIEF DESCRIPTION OF THE DRAWINGS

The drawings described herein are intended to provide a further understanding of the present application and form a part of the present application, and do not constitute a limitation of the present application. In the accompanying drawings:

FIG. 1 is a flow chart for building situational awareness scenes according to an embodiment of the present application.

DETAILED DESCRIPTION

Figure 2:
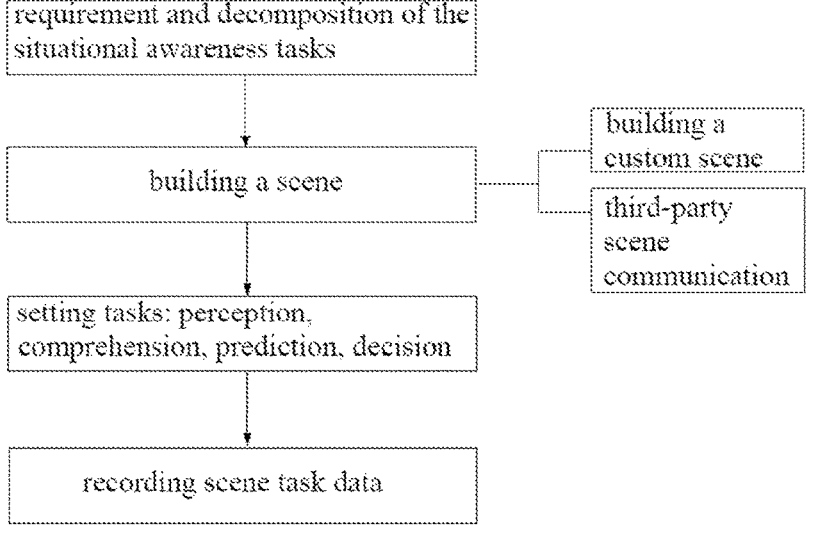
FIG. 2 is a flow chart for building situational awareness scenes according to an embodiment of the present application.

The present application provides a system of combining an evaluation with a training process to a personnel situational awareness evaluation and training, which application scenes are flexible, and the situational awareness evaluation is scientific and reasonable. The scheme can combine a virtual reality technology, a simulation technology, a sensor technology and so on to evaluate the situational awareness of specific personnel under different scenes, and evaluate the results of the situational awareness, perform situational awareness training according to evaluation results of the situational awareness.

The purpose of the present application is to improve a performance of the personnel situational awareness related detection, evaluation, training, and other aspects, thereby improving a situational awareness ability of specific personnel in facing special environments, wherein the specific personnel include but are not limited to pilots, astronauts, drivers, athletes, and relevant operators of a submarine, a tower etc., involving related fields and directions of military industry and national defense, aerospace, driver, sport, intelligent cabin etc.

In order to solve a scene limitation and problem for an existing method of the personnel situational awareness evaluation and training, the present application provides a method of personnel situational awareness evaluation and training, the method adopts the virtual reality technology, the simulation technology, and the sensor technology to evaluate and train the situational awareness for special personnel in special situations, and evaluate the results of the situational awareness evaluation and training, and go over according to the evaluation result.

Figure 1:
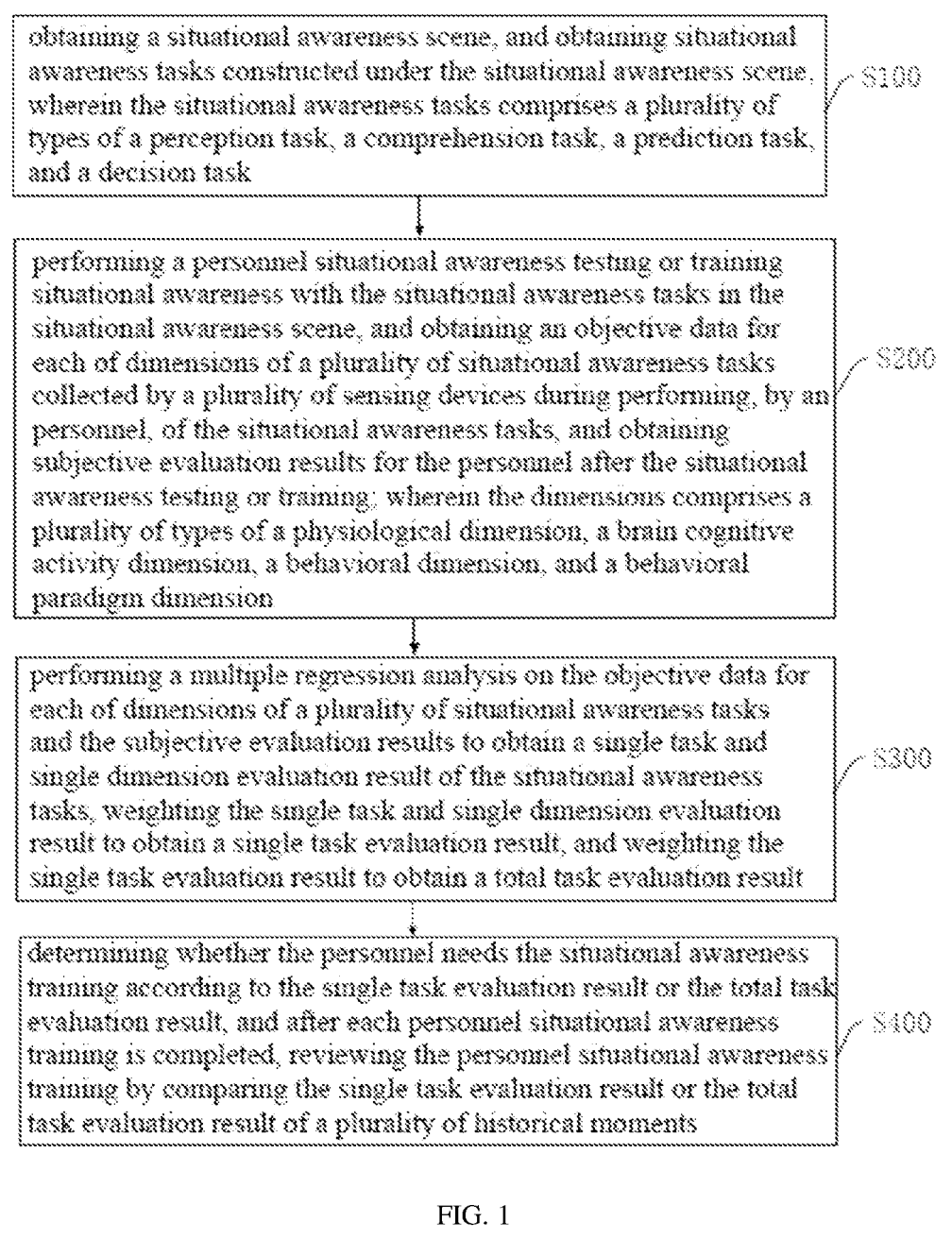

FIG. 1 is a schematic view of the method for assessing and training personnel situational awareness, which comprises the following steps.

Step 100: obtaining a situational awareness scene, and obtaining situational awareness tasks constructed under the situational awareness scene, wherein the situational awareness tasks comprises a plurality of types of a perception task, a comprehension task, a prediction task, and a decision task.

Wherein, the obtaining the situational awareness scene comprises building a custom scene or importing a third-party scene via a communication interface. In some embodiments, the third-party scene can be a simulated scene. The step of obtaining the situational awareness task in the situational awareness scene, by importing the situational awareness task in the situational awareness scene, or customizing the situational awareness task, or importing the behavioral paradigm that contains the situational awareness task. The imported situational awareness task is pre edited and set data by relevant technical personnel, customizing the situational awareness task is a data setting by relevant technical personnel combined with the specific scene, for example, in the evaluation and training of the situational awareness in pilots' perception of the surrounding environment, for customized settings of the situational awareness task in the situational awareness scene, it is necessary to set an emergency hedging task and an engine failures response etc. The behavioral paradigm is a standardized and normalized situational awareness scene, which includes the situational awareness task.

FIG. 2 is a flow chart for building a situational awareness scene according to an embodiment of the present application. First, professional personnel should define requirements of the situational awareness task and resolve the situational awareness tasks to define the required situational awareness scene and the situational awareness task in the situational awareness scene. The system obtains the scene built by professional personnel, a source of the scene is a custom scene built by professional personnel based on the professional knowledge, or the third-party scene imported via the communication interface. The situational awareness task obtained by the system is imported via the situational awareness scene or customized, and the situational awareness task data is recorded. Wherein, the situational awareness task includes the perception task, the comprehension task, the prediction task, and the decision task.

A method for building the situational awareness scene provided by the present application has diverse scenes, rich applicable objects, and can perform targeted and quantitative evaluation and training on different dimensions of the situational awareness. Wherein, the applicable objects include but are not limited to pilots, astronauts, drivers, athletes, and relevant operators of the submarine, the tower etc., and the fields involved include military industry and national defense, aerospace, driver, sport, intelligent cabin.

The steps for obtaining the situational awareness scene enable flexible replacement of applicable scene, expanding an application scope of the present application.

In an embodiment of the present application, a pathway for obtaining the situational awareness task by the system further includes the imported a behavior paradigm containing the situational awareness task.

Furthermore, the customizing the situational awareness tasks comprises a full task setting and a single task setting; the full task setting comprises setting all of the situational awareness tasks at a freezing time point, and the single task setting comprises setting one of the situational awareness tasks at a freezing time point; and wherein, the freezing time point is a time point at which the situational awareness scene is paused for customizing the situational awareness tasks, number of the freezing time points is set to be one or more. The customizing of the situational awareness task makes the setting of the situational awareness scene for the situational awareness evaluation and training more flexible and adjusts an intensity flexibly according to the specific situation of the evaluation and the training, making the evaluation result more accurate or the training effect better.

Specifically, the perception task comprises perceiving information of the situational awareness scene, and recording an initial state of the information of the situational awareness scene at a time of setting the perception task; the comprehension task comprises comprehending the information of the situational awareness scene, recording a correct option by obtaining a selection of custom setup question options at a time of setting the comprehension task; the prediction task includes predicting the information of the situational awareness scene at a future moment and recording the information of the situational awareness scene at the future moment; the decision task includes making a decision for the information of the situational awareness scene and making a selection based on customized decisions. With the above situational awareness tasks, it is possible to cover categories of the situational awareness tasks required for the personnel situational awareness evaluation and training in a vast majority of the application scenes.

Step 200: performing a personnel situational awareness testing or training situational awareness with the situational awareness tasks in the situational awareness scene, and obtaining an objective data for each of dimensions of a plurality of situational awareness tasks collected by a plurality of sensing devices during performing, by a personnel, of the situational awareness tasks, and obtaining subjective evaluation results for the personnel after the situational awareness testing or training; wherein the dimensions comprises a plurality of types of a physiological dimension, a brain cognitive activity dimension, a behavioral dimension, and a behavioral paradigm dimension.

The above performing of situational awareness testing or training for the personnel with the situational awareness task in the situational awareness scene, a presentation of the situational awareness scenes is achieved with the virtual reality technology, the simulation technology, augmented reality technology, and/or mixed reality technology.

Figure 3:
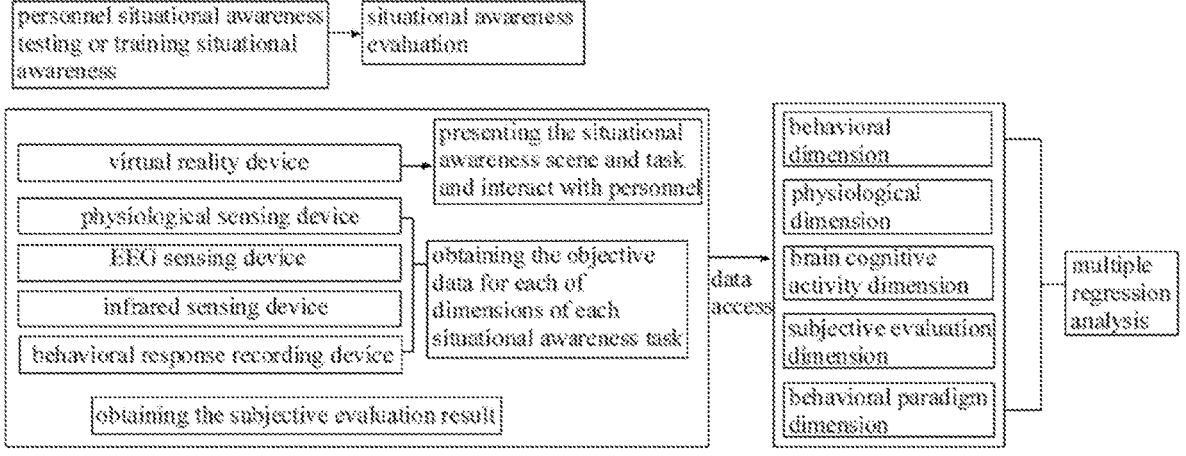
FIG. 3 is a flow chart of a situational awareness evaluation according to an embodiment of the present application.

FIG. 3 is a flow chart of the situational awareness evaluation according to an embodiment of the present application. Collecting the objective data for each dimension of each situational awareness task based on the sensing device, wherein, the sensing device includes a physiological sensing device, an EEG sensing device, an infrared sensing device and a behavioral response recording device. Correspondingly, the dimension of the objective data for each dimension of the situational awareness task includes the following: the physiological dimension, the brain cognitive activity dimension, the behavioral dimension, and the behavioral paradigm dimension. Combining the subjective evaluation result obtained by the personnel, the objective data and the subjective evaluation result of each dimension is obtained, and multiple regression analysis is performed on the objective data and the subjective evaluation result of each dimension.

In an embodiment of the present application, an object of the situational awareness testing further includes the behavioral paradigm, which is the situational awareness scene containing a situational awareness task paradigm by referring to relevant literature in the field, the situational awareness scene of the behavioral paradigm contains corresponding situational awareness tasks, which can be embedded in the system for the situational awareness evaluation and training.

In an embodiment of the present application, before performing the personnel situational awareness training, the method further includes obtaining a frequency of the personnel situational awareness training, the frequency of the situational awareness training and a number of training groups implemented each time can be set by a person. Making the intensity of the situational awareness training adjustable, and an entire process of the situational awareness training is more meet to the needs of users.

Step 300: performing a multiple regression analysis on the objective data for each of dimensions of a plurality of situational awareness tasks and the subjective evaluation results to obtain a single task and single dimension evaluation result of the situational awareness tasks, weighting the single task and single dimension evaluation result to obtain a single task evaluation result, and weighting the single task evaluation result to obtain a total task evaluation result.

The method provided in the present application, quantifies the situational awareness of the personnel in dimensions such as perception, comprehension, prediction and decision with different situational awareness tasks, including the perception task, the comprehension task, the prediction task, and the decision task, and provides a feedback and training according to the quantified situational awareness evaluation result.

Wherein, the dimension of the single task and single dimension evaluation result includes but is not limited to the behavioral dimension, the physiological dimension, the brain cognitive activity dimension, the behavioral paradigm dimension and subjective evaluation dimension, referring to FIG. 3.

Figure 4:
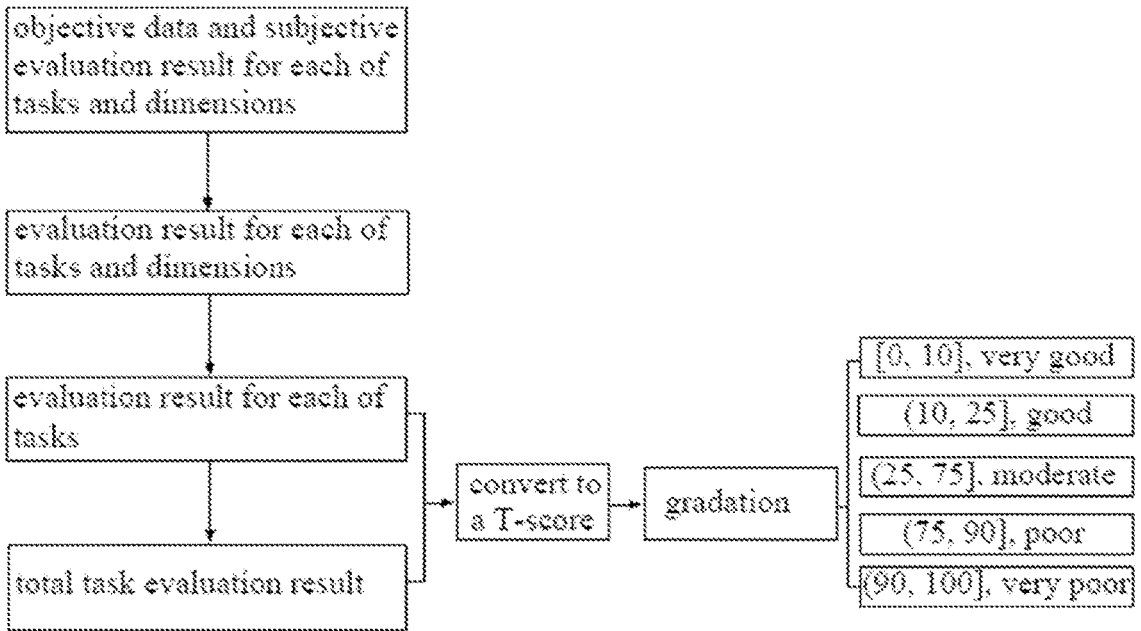
FIG. 4 is a process of analyzing situational awareness evaluation data according to an embodiment of the present application.

FIG. 4 is a process of analyzing situational awareness evaluation data according to an embodiment of the present application. The single task and single dimension evaluation result is obtained by weighting the objective data and subjective evaluation result based on each dimension of each task, the single task evaluation result is obtained by weighting the single task and single dimension evaluation result, based on the single task evaluation result, the total task evaluation result is obtained. The single task evaluation result or the total task evaluation result can be converted to a T-score, and graded based on the T-score, wherein, very good [0, 10], good (10, 10], moderate (25, 75], poor (75, 90], and very poor (90, 100]. The evaluation result is presented in the form of a grade to make the evaluation result more intuitive.

Step 400: determining whether the personnel needs the situational awareness training according to the single task evaluation result or the total task evaluation result, and after each personnel situational awareness training is completed, reviewing the personnel situational awareness training by comparing the single task evaluation result or the total task evaluation result of a plurality of historical moments.

Figure 5:
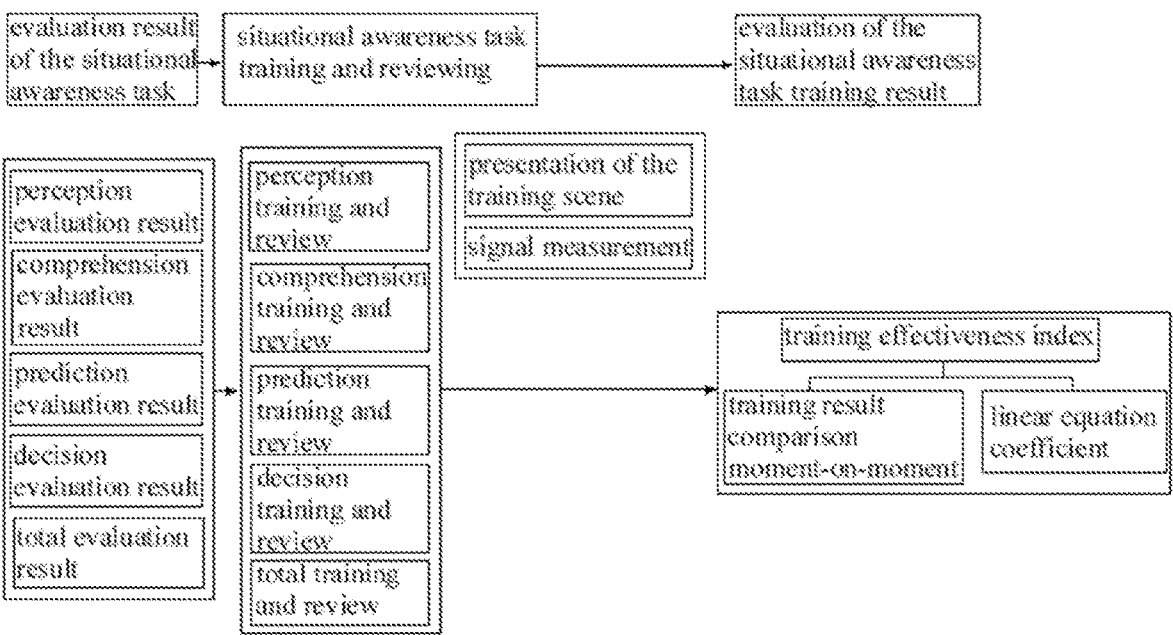
FIG. 5 is a process of a situational awareness training according to an embodiment of the present application.

FIG. 5 is a process of the situational awareness training according to an embodiment of the present application. Performing the situational awareness training and review for the personnel below the single task evaluation result (including perception evaluation results, comprehension evaluation results, prediction evaluation results, and decision evaluation results) or the total task evaluation result that is preset. Wherein reviewing the step of the personnel situational awareness training to train a validity index, which includes a comparison of training results or a linear equation coefficient to present. Wherein, the single task evaluation result include the perception evaluation result, the comprehension evaluation result, the prediction evaluation result, and the decision evaluation result. Correspondingly, the personnel situational awareness training and review include perception training and review, comprehension training and review, prediction training and review, decision training and review, and total training and review. The dimensions included in the single task evaluation results are only examples, and the present application is not limited to this.

The reviewing the personnel situational awareness training by comparing the single task evaluation result or the total task evaluation result at the plurality of historical moments includes reviewing the personnel situational awareness training by calculating the training result comparison moment-on-moment and reviewing the personnel situational awareness training with the linear regression coefficient. The personnel situational awareness training is reviewed by calculating the training result comparison, which is expressed by a formula of:

C represents a training evaluation result comparison moment-on-moment for each task or the total task, $$E_i'$$

is a training evaluation result of each task or the total task for an i-th training, a calculation of $$E_i'$$

is consistent with a calculation, by a situational awareness evaluation module, of the single task evaluation result or the total task evaluation result. In particular, when i=1, $$E_{i-1}' = E.$$

In an embodiment of the present application, the linear regression coefficient is the coefficient calculated with an univariate linear regression equation for the training evaluation result comparison of each task or the training evaluation result of the total task, which is expressed by the formula as follows:

$$E' = (\Sigma z' ET) + b';$$

In particular, E' is a dependent variable, which is a target we want to train, z' is the linear regression coefficient, ET is the single task evaluation result obtained from each training, and b' is an intercept. The linear regression coefficient represents a slope of the univariate equation, and the larger the numerical value, the better the training effect.

In an embodiment of the present application, the method further includes grading the total task evaluation result and performing the situational awareness training for the personnel below a preset level.

For example, the customized scene in step 100, the scene is built by setting the relevant information of the situational awareness scene and the characteristics of each object (such as a motion trajectory, a wind speed and a flight angle in the scenes of the pilot situational awareness evaluation and training), the related information of the scene include but is not limited to a name, a duration, and the object of the scene. The relevant information of the situational awareness scene can be imported from a system template to a trajectory data of each object, and customized in the system, the relevant key point of each object can be automatically set according to the customized information.

Taking football as an example, the trajectory of each object is set according to the information of a set motion object, as the set duration is 4 seconds, team A: 11 people, red team uniform; team B: 11 people, blue team uniform; goalkeeper: yes, judge: yes; set the trajectory of each object according to the information of the settings. The system can drag corresponding personnel to a certain position in a middle of the field as a starting position as needed, and set a number and a role of a team member (the role can be selected as ball holder, player, judge, and goalkeeper according to the settings, and the other three roles have an uniqueness except for the player, after selecting a certain object, other objects cannot be selected). After setting the personnel information, setting a customized trajectory, a key frame for each step, coordinates X, Y, and an angle orientation. After setting the trajectory, it can be viewed. When setting the situational awareness scenes, different switching perspectives can be set to preview and experience with different perspectives.

In step 100, the situational awareness task includes the plurality of types of the perception task, the comprehension task, the prediction task, and the decision task. Wherein: the perception task includes perceiving an information of the situational awareness scene, and recording an initial state of the situational awareness scene information at the time of setting the perception task, including relative information of each object in the situational awareness scenes; the comprehension task includes understanding the information of the situational awareness scene, recording a correct option by obtaining a selection of custom setup question options at the time of setting the comprehension task; the prediction task includes predicting the information of the situational awareness scene at a future moment and recording the information of the situational awareness scene at the future moment, optionally, the system supports a predicted time point after customizing the freezing time; the decision task includes making a decision for the information of the situational awareness scene and making a selection based on customized decisions, and recording the correct option for the decision task by the system.

The perception task, the comprehension task, the prediction task, and the decision task in a simulated combat scene are explained with examples:

1. the perception task: perceiving the change of a current state on the field. During a process of a simulated combat, a certain time point is frozen, and all the active content on the field disappears to an edge of the field, it is necessary to restore the corresponding content as much as possible to the state before it disappeared, a performance of the perception task should be judged according to coordinate positions, directions and angles restored by the corresponding content.

2. the comprehension task: comprehending a form of the current state on the field. During the process of the simulated combat, the certain time point is frozen, correctly comprehending and selecting tactical and strategic objectives of the activities on the field as a judgment of the performance of the comprehension task.

3. the prediction task: predicting the change of the state on the field at a next time point. During the process of the simulated combat, the certain time point is frozen, the predicted time point is set after the time point is frozen at the same time, the state of the predicted time point which is set needs to be predicted according to the current state of the freezing time point, there are two forms, one is to predict the coordinate positions, directions and angles corresponding to the content on the field of the predicted point as the performance of the prediction task, the other is to correctly analyze and select the tactical and strategic objectives of the activities on the field of the predicted point as the judgment of the performance of the predicted task.

4. the decision task: determining a next execution plan according to the current scene state. During the process of the simulated combat, the certain time point is frozen, according to the selected task object, the execution of the next task is determined and selected, and the corresponding score for the decision selection is configured as the performance of the decision task.

Figure 6:
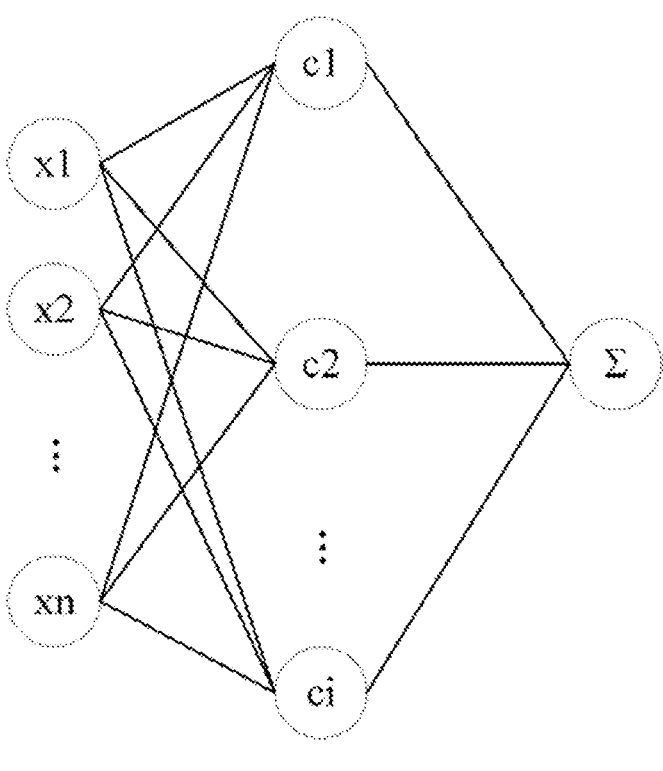
FIG. 6 is a schematic view of a topology structure of a situational awareness task decision model according to an embodiment of the present application.

FIG. 6 is a schematic view of a topology structure of the situational awareness task decision model according to an embodiment of the present application, including an input layer, a hidden layer and an output layer. In step 100, the method further includes: obtaining the situational awareness task decision model obtained with an expert evaluation, which is a machine learning neural network with a radial basis function (RBF) as an activation function; the situational awareness scene containing the situational awareness task as the input layer is input into the situational awareness task decision model, the situational awareness scene containing the situational awareness task is a figure-data structure storage mode $(x1, x2, \ldots, xn$ in FIG. 6), the hidden layer performs an optimal decision processing on the data structure based on an RBF algorithm, obtains $c1, c2, \ldots,$ $ci$ in FIG. 6 with different combinations, and outputs the optimal decision $\Sigma$ of the situational awareness task. Combining the machine learning or deep learning techniques to optimize situational awareness tasks, making them more representative.

In an embodiment of the present application, the dimension of the objective data for each task and each dimension includes the behavioral dimension, the physiological dimension, the brain cognitive activity dimension and the behavioral paradigm dimension. The dimension of the single task and single dimension evaluation result includes the behavioral dimension, the physiological dimension, the brain cognitive activity dimension, the behavioral paradigm dimension and subjective evaluation dimension.

In an embodiment of the present application, before performing the personnel situational awareness training, the method further includes obtaining the frequency of the personnel situational awareness training, for example, performing the situational awareness training for the personnel in addition to the "very good" level, training one group every day, with each group training three times.

In an embodiment of the present application, the situational awareness scene and the situational awareness task are presented based on the virtual reality technology, the data of the presented situational awareness scene is one or more, and the number of the presented situational awareness task is one or more, the system can repeatedly present a single situational awareness task.

In step 200, the sensing device collects the objective data for each dimension of each situational awareness task, including but not limited to: 1. physiological data: skin electrical data, skin temperature data, heart rate variability, and high and low pressure; 2. behavioral data: reaction time, accuracy, effective range of response, and total score of the task; 3. brain cognitive activity data: EEG data, $\alpha/\beta$ and near-infrared data; 4. behavioral paradigm data: perception, working memory and direction discrimination.

In step 300, the steps of the multiple regression analysis based on the objective data and the subjective evaluation result of each dimension of each situational awareness task, which are expressed by the formula as follows:

1. obtaining the single task and single dimension evaluation result $$ED = (\Sigma a \cdot ESD) + b_1.$$

In particular, ED is the single task and single dimension evaluation result, that is, the result of the task dimension we want to predict, a is a weight of each dimension of each task, ESD is an indicator of each task dimension, and $b_1$ is the intercept.

2. obtaining the single task evaluation result $$ET = (\Sigma w \cdot ED) + b_2.$$

In particular, ET is the single task evaluation result, which is the result of the task we want to predict, w is the weight of each task, ED is the single task and single dimension evaluation result, and $b_2$ is the intercept.

3. obtaining the total task evaluation result $$E = (\Sigma z \cdot ET) + b_3.$$

In particular, E is the evaluation result of each total task, which is the total result we want to predict, z is the weight of each task, ET is the evaluation result of the single task, and $b_3$ is the intercept.

4. optionally, converting the evaluation result into the T-score (a normal distribution with an obey mean of 50 and a standard deviation of 10)

Calculating the T-score of each task evaluation result or the total task evaluation result based on a norm mean and the standard deviation, and evaluating based on a range of the T-score value. Wherein the standard for dividing the T-score are: very good [0, 10], good (10, 25], moderate (25, 75], poor (75, 90], very poor (90, 100].

In an embodiment of the present application, in step 400, the linear regression coefficient is the coefficient calculated by the univariate linear regression equation for the training evaluation result comparison of each task or the training evaluation result of the total task, which is expressed by the formula as follows:

$$E' = (\Sigma z' ET) + b';$$

In particular, E' is the dependent variable, which is the target we want to train, z' is the linear regression coefficient, ET is the single task evaluation result obtained from each training, and b' is the intercept. The linear regression coefficient represents the slope of the univariate equation, and the larger the numerical value, the better the training effect.

The specific calculation method is to obtain the results of the first training and the second training (two different ET) firstly, calculate z and b based on E and the two different ET, and then calculate new z' and b' based on the results of the second training and the third training the larger z', the better the training effect.

It should be understood that in addition to the multiple regression analysis method mentioned above, the present application can also adopt other methods to obtain the total task evaluation result from the objective data and the subjective evaluation result. For example, with a mathematical model which is established in advance, the objective data and the subjective evaluation results are substituted into the model to calculate the total task evaluation results. In another example, with the machine learning, a machine learning model is trained with a large amount of the objective data and the subjective evaluation results annotated with the total task evaluation results, after training, the objective data and the subjective evaluation results of the personnel to be evaluated are input into the trained machine learning model to obtain the total task evaluation result.

The present application relates to the method, system and storage medium of the personnel situational awareness evaluation and training, by obtaining different situational awareness scenes and the situational awareness tasks to flexibly change the scene, obtaining a comprehensive score by progressively evaluating the results of the single task and single dimension evaluation, the single task evaluation, and the total task evaluation, achieving a scientific and reasonable evaluation of the personnel situational awareness, and combining the process of the evaluation and training, effectively expanding a functionality and application scope of the system.

Correspondingly to the above method, the present application further provides the system of the personnel situational awareness evaluation and training, which includes a computer device, the computer device includes a processor and a memory, and computer instructions are stored in the memory, and the processor is configured to implement the computer instructions stored in the memory, when the computer instructions are implemented by the processor, the system implements the steps of the above method.

The system of the personnel situational awareness evaluation and training based on a virtual reality interaction technology includes a situational awareness scene building module, a personnel situational awareness evaluation module, a personnel situational awareness training module and a situational awareness data management module. The situational awareness data management module is configured to manage a building data of the situational awareness scene building module, an evaluation data of the situational awareness evaluation module, and a training data of the situational awareness training module.

The embodiment of the present application further provides a computer-readable storage medium, on which a computer program is stored, when the computer program is implemented by the processor, the steps of the above edge computing server deployment method are implemented. The computer-readable storage medium can be a tangible storage medium, such as random access memory (RAM), main memory, read-only memory (ROM), electrically programmable ROM, electrically erasable programmable ROM, register, floppy disk, hard disk, removable storage disk, CD-ROM, or any other forms of the storage medium well-known in the technical field.

Those skilled in the art should understand that the exemplary components, systems, and methods described in conjunction with the disclosed embodiments in the present application can be implemented in hardware, software, or a combination of the two. Whether to implement it in hardware or software depends on the specific application and design constraint of the technical solution. Professional technicians may use different methods to implement the described functions for each specific application, but the implementation should not be considered beyond the scope of the present application. When implemented in hardware, for example, it can be, electronic circuit, application specific integrated circuit (ASIC), appropriate firmware, plug-in, function card etc. When implemented in software, the elements of the present application are programs or code segments configured to implement the required tasks. The programs or code segments can be stored in a machine-readable medium, or transmitted on transmission mediums or communication links with data signals carried by carriers.

What is claimed is:

1. A method for assessing and training personnel situational awareness for quantifying personnel situation awareness, comprising:

obtaining a situational awareness scene by building a custom scene or importing a third-party scene via a communication interface, and obtaining situational awareness tasks constructed under the situational awareness scene, wherein the situational awareness tasks comprise multiple ones among a perception task, a comprehension task, a prediction task, and a decision task;

performing personnel situational awareness testing or personnel situational awareness training via virtual reality equipment based on the situational awareness tasks in the situational awareness scene, wherein a presentation of the situational awareness scene is achieved with virtual reality technology, simulation technology, augmented reality technology, or mixed reality technology, and obtaining subjective evaluation results for personnel after the personnel situational awareness testing or the personnel situational awareness training;

obtaining objective data across a plurality of dimensions for each of a plurality of situational awareness tasks collected by a plurality of sensing devices during personnel execution of the situational awareness tasks, wherein the plurality of sensing devices comprise a physiological sensing device, an electroencephalogram (EEG) sensing device, an infrared sensing device, and a behavioral response recording device, and the plurality of dimensions comprise multiple ones among a physiological dimension, a brain cognitive activity dimension, a behavioral dimension, and a behavioral paradigm dimension;

performing multiple regression analysis on the objective data of each of the plurality of dimensions for each of the plurality of situational awareness tasks and the subjective evaluation results to quantify the personnel situation awareness, thereby obtaining single task and single dimension evaluation result of one of the situational awareness tasks, calculating a single task evaluation result by weighting respective single task and single dimension evaluation results, and calculating a total task evaluation result, wherein:

obtaining the single task and single dimension evaluation result is performed according to a formula:

$$ED=(\Sigma a \cdot ESD)+b_1$$

wherein ED is the single task and single dimension evaluation result, a is a weight of each dimension of each task, ESD is an indicator of each task dimension, and b1 is an intercept;

calculating the single task evaluation result is performed according to a formula:

$$ET=(\Sigma w \cdot ED)+b_2$$

wherein ET is the single task evaluation result, w is a weight of each task, ED is the single task and single dimension evaluation result, and b2 is a second intercept;

calculating the total task evaluation result is performed according to a formula:

$$E=(\Sigma z \cdot ET)+b_3$$

wherein E is the total task evaluation result, z is a second weight of each task, ET is the single task evaluation result, and b3 is a third intercept;

converting the single task evaluation result or the total task evaluation result into a T-score having a normal distribution with a mean of 50 and a standard deviation of 10; and determining whether the personnel needs situational awareness training according to the single task evaluation result or the total task evaluation result, and after each personnel situational awareness training is completed, reviewing the personnel situational awareness training by comparing the single task evaluation result or the total task evaluation result of a plurality of historical moments, comprising: reviewing the personnel situational awareness training by calculating a training result comparison moment-on-moment with a formula of:

$$C = (E_i' - E_{i-1}')/E_{i-1}' * 100\%$$

wherein C represents a training evaluation result comparison moment-on-moment for each task or total tasks that quantifies changes in results of the personnel situational awareness training, $$E_i'$$

is a training evaluation result or each task or a total task for an i-th training obtained through the multiple regression analysis.

2. The method according to claim 1, wherein the obtaining the situational awareness tasks constructed under the situational awareness scene comprises, in the situational awareness scene, importing the situational awareness tasks, or customizing the situational awareness tasks, or importing a behavioral paradigm that contains the situational awareness scene.

3. The method according to claim 2, wherein the customizing the situational awareness tasks comprises a full task setting and a single task setting; the full task setting comprises setting all of the situational awareness tasks at a freezing time point, and the single task setting comprises setting one of the situational awareness tasks at the freezing time point; and wherein, the freezing time point is a time point at which the situational awareness scene is paused for customizing the situational awareness tasks, and a number of the freezing time points is set to be one or more.

4. The method according to claim 1, wherein,
the perception task comprises perceiving information of the situational awareness scene, and recording an initial state of the information of the situational awareness scene at a time of setting the perception task;

the comprehension task comprises comprehending the information of the situational awareness scene, and recording a correct option by obtaining a selection of custom setup question options at a time of setting the comprehension task;

the prediction task comprises predicting the information of the situational awareness scene at a future moment and recording the information of the situational awareness scene at the future moment; and the decision task comprises making a decision for the information of the situational awareness scene and making a selection based on customized decisions.

5. The method according to claim 1, wherein the method further comprises:

inputting the situational awareness scene containing the situational awareness tasks as an input layer into a situational awareness task decision model, and outputting an optimal decision of the situational awareness tasks.

6. The method according to claim 5, wherein before performing the personnel situational awareness training, the method further comprises obtaining a frequency of the personnel situational awareness training; and wherein the method further comprises grading the total task evaluation result and performing the personnel situational awareness training for the personnel below a preset level.

7. The method according to claim 1, wherein, the reviewing the personnel situational awareness training by comparing the single task evaluation result or the total task evaluation result at the plurality of historical moments further comprises: reviewing the personnel situational awareness training by calculating a linear regression coefficient based on the training evaluation result comparison moment-on-moment for each task or the total task by using an univariate linear regression equation, represented by a formula:

$$E'=(\Sigma z' \cdot ET')+b';$$

wherein E' is a dependent variable, which represents a target to be trained, z' is the linear regression coefficient which represents training effect, ET' is the single task evaluation result obtained from each training, and b' is a fourth intercept.

8. A system for assessing and training personnel situational awareness, comprising: a processor and a memory, wherein the memory is configured to store computer instructions, the processor is configured to execute the computer instructions stored in the memory, and the system is configured to implement the method according to claim 1 when the computer instructions are executed by the processor.

9. A non-transitory computer-readable storage medium with a computer program stored thereon, wherein the computer program is configured to be executed by a processor to implement the method according to claim 1.

* * * * *